United States Patent [19]

Udart

[11] 4,013,892
[45] Mar. 22, 1977

[54] IR GENERATOR HAVING ELLIPSOIDAL AND PARABOLOIDAL REFLECTORS
[75] Inventor: John Charles Udart, Byron, N.Y.
[73] Assignee: Sybron Corporation, Rochester, N.Y.
[22] Filed: Jan. 29, 1973
[21] Appl. No.: 327,692
[52] U.S. Cl. .............................. 250/504; 250/495
[51] Int. Cl.² .......................................... G01J 1/00
[58] Field of Search .......... 250/493, 494, 496, 503, 250/504, 495; 240/41.35; 350/294, 292, 293

[56] References Cited
UNITED STATES PATENTS
3,784,836  1/1974  Tolliver ........................... 250/495

Primary Examiner—Davis L. Willis
Attorney, Agent, or Firm—Theodore B. Roessel; Joseph C. MacKenzie

[57] ABSTRACT

An infrared generator wherein an ellipsoidal reflector has a source rich in infrared radiation at one focus thereof. The end of the reflector at the other focus merges with a paraboloidal reflector positioned so that the focus of the latter reflector coincides with the said other focus of the former. The axes of the reflectors intersect at right angles to each other.

4 Claims, 3 Drawing Figures

IR GENERATOR HAVING ELLIPSOIDAL AND PARABOLOIDAL REFLECTORS

RELATED APPLICATION

Applications S.N. 295,421 and 327,693 for U.S. Pat. of Peter Marvin Tolliver, filed 6 Oct. 1972 and 29 Jan., 1973, both assigned to the assignee hereof, and entitled "IR Generator Having Ellipsoidal and Paraboloidal Reflectors."

FIELD OF THE INVENTION

The present invention generally relates to measuring the properties or the nature of a given material as a function of the interaction of said material with infrared (IR) radiation. More particularly, the present invention relates to generating the IR radiation both efficiently and suitable for measuring moisture content of paper web by subjecting the paper to the infrared radiation and detecting the effect of moisture in the paper on the radiation. Measuring systems of the sort contemplated here are typified by the system described and claimed in U.S. Pat. No. 3,551,678 to Richard L. Mitchell.

DESCRIPTION OF THE PRIOR ART

Prior art IR radiation generators in the systems known to me are highly inefficient. Because the basic signal to noise ratio of a system is determined by the generator, such inefficiency is a major source of difficulty in designing a system which will be simultaneously suitable for on-line use of controlling industrial processes, and at the same time accurate.

It is the object of the present invention to provide, in a system of the Mitchell type, a novel high-efficiency IR radiation generator, so efficient as to increase markedly the measuring capability of the system and, simultaneously, to simplify the system and make it more rugged. It is also a particular object of the invention to provide an IR radiation generator which is efficient, light and compact, is easy and inexpensive to construct, and yet is simple in design, durable and rugged.

SUMMARY OF THE INVENTION

According to the present invention, the novle IR radiation generator comprises an ellipsoidal reflective shell in combination with a paraboloidal reflective shell, there being an IR-rich source of radiation at one ellipse focus, and the major and principal axes of the shells intersecting at right angles to each other. The source IR radiation is collected by the elliposoidal shell and the collected radiation is collimated by the paraboloidal shell.

In use according to the aforesaid Mitchell patent, the collimated IR is filtered to produce IR beams having well-defined spectral content. The beams are directed on the paper, or other material, and the system senses what remains of the beams after they have interacted with the paper, and then computes some property or characteristic of the material, for example, moisture content of the paper, that is to say, the percent by weight of liquid water contained in that portion of the paper irradiated by the IR beams. In the present invention, 70% or more of the IR from the source is collimated and presented for filtering.

DESCRIPTION OF THE PREFERRED EMBODIMENTS

Figure 1:
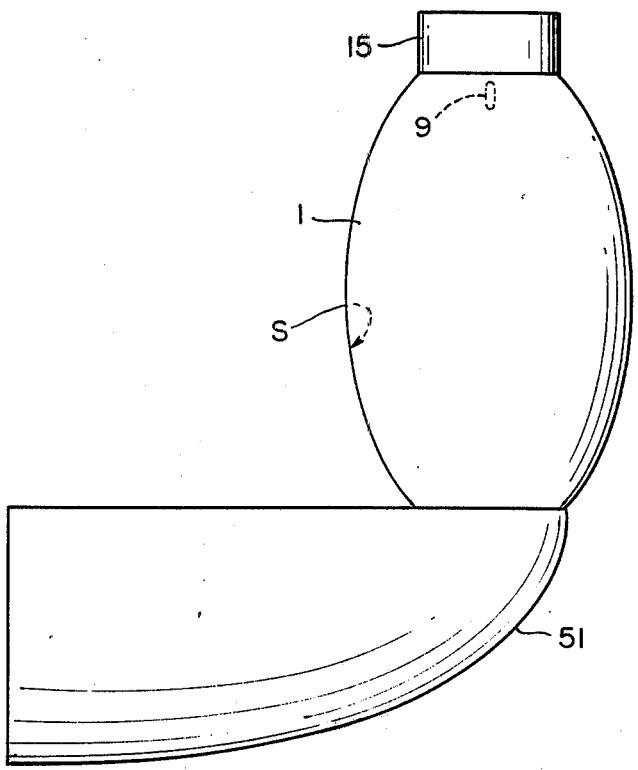
FIG. 1 is a side elevation, of an IR generator according to the invention.
Figure 2:
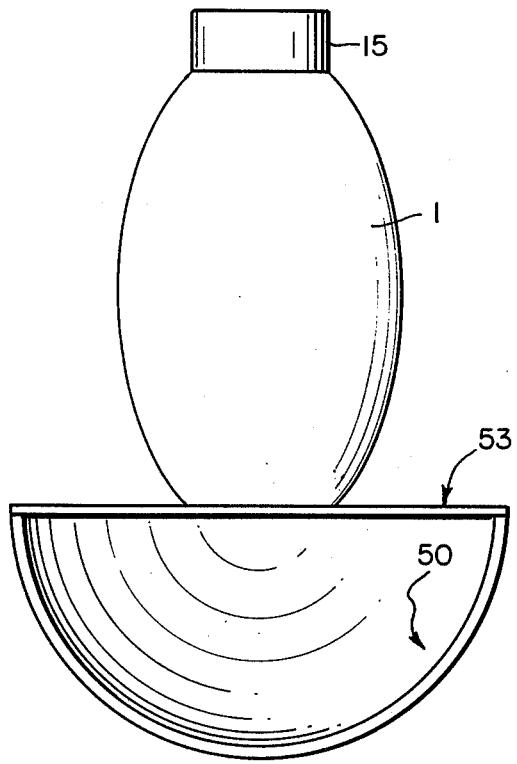
FIGS. 2 and 3 are an opposing end elevation and a plan view, respectively, of the IR generator of FIG. 1.
Figure 3:
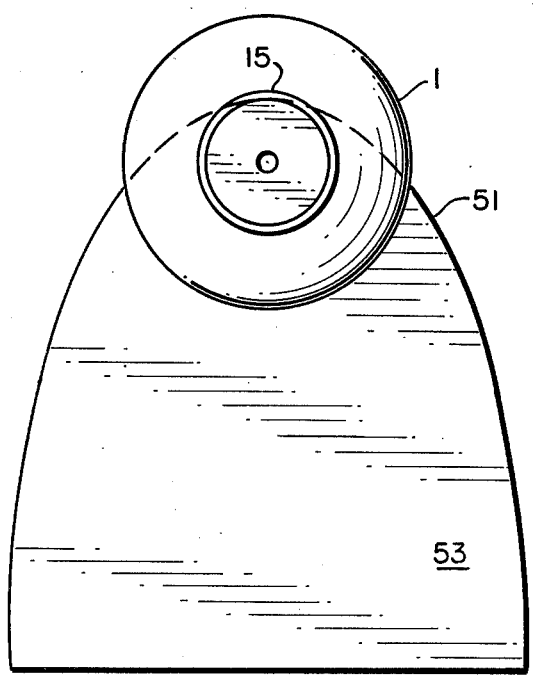

In FIG. 1, reference numeral 1 denotes a shell having internal reflecting surface S coincident with an ellipsoidal surface of revolution of a plane ellipse about its major axis. As will be seen from FIGS. 1, 2, and 3, the shell corresponds to the surface truncated at both ends.

One focus of the ellipse is the effective locus of a filament 9, which forms part of a suitable lamp (not shown), which is supported in any suitable manner (not shown) by structure 15 terminating the shell 1.

For present purposes, filament 9 may be supposed to be an IR-rich source, when electrically energized to incandescence, as for example, in a quartz-iodine lamp, or equivalent. The purpose of the structure thus far described is to reproduce, so to speak, the radiation from the filament, at the other focus of the shell 1.

Supposing the surface S to be perfectly smooth and reflective with respect to the desired spectral content of the radiation from filament 9, then it is immediately obvious that when the filament incandesces, a great deal of the resultant radiation will be reflected substantially to said other focus of shell 1 in practice around 70%. Naturally, for maximum efficiency optimum finish of reflecting surfaces is required. Thus, in the present case, the spectral range of interest went down to 1.8 micron wave-length. In order to achieve specular reflection at this wave-length, a 4 micron layer of gold was plated on surface S after the surface, originally produced by machining it out of a cylinder of brass, had been smoothed as much as possible by machining, buffing and the like.

According to the present invention, the radiation from the image source formed at said other focus of shell 1 is collimated by a paraboloidal shell, the principal axis of which is at a right angle thereto.

Thus, in FIG. 1 a shell 51 is coupled to shell 1, shell 51 having an internal reflecting surface 50 in the form of part of a paraboloidal surface of revolution corresponding to a parabola the principal axis of which is transverse to the major axis of shell S.

Shell 51 collimates the radiation from, in effect, the upper focus of shell 1. Due to the orientation of the principal axis 51, up to about 70% of the radiation reflected from the surface 50 can be collimated. The shell 51 is semi-paraboloidal, being completed by a flat plate 53 having an aperture (not shown) for permitting the radiation from the shell 1 to enter the shell 51. Shell 1 is fixed to the plate 53 and over said opening by any suitable means (not shown).

Having described my invention as required by the statutes, I claim:

1. In an IR generator, the combination of a first shell having an inner reflective ellipsoidal surface dand a second shell having an inner reflective paraboloidal surface;
    said shells being secured together with said surfaces' respective major and principal axes transverse to each other;
    said first shell being adapted for providing a source of radiation at one focus of said ellipsoidal surface and said shells having openings where they are secured together, for allowing said radiation to enter said second shell via the other focus of said ellipsoidal surface;

said paraboloidal surface being a semiparaboloid, one side of which has a flat plate having one of said openings therein.

2. The invention of claim 1, wherein said axes are substantially perpendicular to each other.

3. In an IR generator, the combination of a first shell having an inner reflective ellipsoidal surface and a second shell having an inner reflective paraboloidal surface;

said shells being secured together with said surfaces' respective major and principal axes transverse to each other;

said first shell being adapted for providing a source of radiation at one focus of said ellipsoidal surface and said shells having openings where they are secured together, for allowing said radiation to enter said second shell via the other focus of said ellipsoidal surface;

said first shell having its said opening defined by having the end thereof at said one focus truncated, and said second shell being a semiparaboloid having a flat plate to which the last said end is secured.

4. The invention of claim 3, where said axes are substantially perpendicular to each other.

* * * * *